US009797868B2

United States Patent
Macleod et al.

(10) Patent No.: US 9,797,868 B2
(45) Date of Patent: Oct. 24, 2017

(54) SYSTEMS AND METHODS FOR DETERMINING GEOLOGIC PROPERTIES USING ACOUSTIC ANALYSIS

(71) Applicants: Gordon Macleod, Houston, TX (US); Robert J. Pottorf, Houston, TX (US); Dennis P. Smith, Baytown, TX (US); Limin Song, West Windsor, NJ (US); Peng Xu, Annandale, NJ (US); Enru Liu, Sugar Land, TX (US)

(72) Inventors: Gordon Macleod, Houston, TX (US); Robert J. Pottorf, Houston, TX (US); Dennis P. Smith, Baytown, TX (US); Limin Song, West Windsor, NJ (US); Peng Xu, Annandale, NJ (US); Enru Liu, Sugar Land, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 0 days.

(21) Appl. No.: 14/295,211

(22) Filed: Jun. 3, 2014

(65) Prior Publication Data

US 2014/0283609 A1    Sep. 25, 2014

Related U.S. Application Data

(63) Continuation of application No. 12/992,844, filed as application No. PCT/US2009/041128 on Apr. 20, 2009, now Pat. No. 8,781,762.

(Continued)

(51) Int. Cl.
*G01N 29/14* (2006.01)
*G01N 3/06* (2006.01)
(Continued)

(52) U.S. Cl.
CPC ............... *G01N 29/14* (2013.01); *G01N 3/06* (2013.01); *G01N 3/08* (2013.01); *G01N 29/045* (2013.01);
(Continued)

(58) Field of Classification Search
CPC .... G01N 3/06; G01N 3/08; G01N 2203/0658; G01N 29/14; G01N 33/24
(Continued)

(56) References Cited

U.S. PATENT DOCUMENTS 3,334,329 A * 8/1967 Fons .............................. 367/28
3,622,969 A * 11/1971 Lebreton et al. ............... 367/30
(Continued)

FOREIGN PATENT DOCUMENTS

WO    WO 02/052243    7/2002
WO    WO 2005/015197    2/2005
(Continued)

OTHER PUBLICATIONS

Graves, R.M., et al., (2002), "Temperatures Induced by High Power Lasers: Effects on Reservoir Rock Strength and Mechanical Properties," *SPE 78154, Rock Mechanics Conf.*, Irving, Texas, Oct. 20-23, 2002, pp. 1-7.
(Continued)

*Primary Examiner* — Mohamed Charioui
(74) *Attorney, Agent, or Firm* — ExxonMobil Upstream Research Company, Law Department (57) ABSTRACT

Systems and methods which determine geologic properties using acoustic analysis are shown. Acoustic signals are collected during processing (e.g., crushing, shearing, striking, compressing, etc.) of geologic media, such as rock samples, for determining geologic properties according to embodiments. The acoustic signals collected may include frequency information, amplitude information, time infor-
(Continued)

mation, etc. which may be utilized in determining geologic properties, such as geologic media properties (e.g., mineralogy, porosity, permeability, sealing capacity, fracability, compressive strength, compressibility, Poisson's Ratio, Youngs Modulus, Bulk Modulus, Shear Modulus), geologic structure properties (e.g., lithology, seal quality, reservoir quality), geologic acoustic properties (e.g., acoustic logging effectiveness, acoustic response, natural or harmonic frequencies, etc.). Embodiments may be used to provide determination of geologic properties from a variety of geologic media samples, such as cuttings, core samples, etc.

17 Claims, 5 Drawing Sheets

Related U.S. Application Data (60) Provisional application No. 61/080,339, filed on Jul. 14, 2008.

(51) Int. Cl.
  *G01N 3/08* (2006.01)
  *G01N 29/04* (2006.01)
  *G01N 29/44* (2006.01)
  *G01N 29/46* (2006.01)
  *G01N 33/24* (2006.01)

(52) U.S. Cl.
  CPC ......... *G01N 29/4427* (2013.01); *G01N 29/46* (2013.01); *G01N 33/24* (2013.01); *G01N 2203/0658* (2013.01); *G01N 2291/0232* (2013.01); *G01N 2291/0289* (2013.01); *G01N 2291/02818* (2013.01); *G01N 2291/02827* (2013.01)

(58) Field of Classification Search
  USPC ............ 702/48, 50, 56, 134, 159, 171, 183; 73/152.18, 152.47, 594, 597, 801
  See application file for complete search history.

(56) References Cited

U.S. PATENT DOCUMENTS

| | | | |
|---|---|---|---|
| 3,719,474 A | | 3/1973 | Bieher et al. |
| 4,107,981 A | * | 8/1978 | Kanagawa et al. ............. 73/801 |
| 4,344,326 A | | 8/1982 | Kahn |
| 4,382,384 A | * | 5/1983 | Mitchell et al. ................ 73/594 |
| 4,762,559 A | | 8/1988 | Penrice et al. |
| 4,806,292 A | | 2/1989 | Delacy |
| 4,882,927 A | | 11/1989 | Gould |
| 4,918,993 A | | 4/1990 | Hughson |
| 4,956,999 A | | 9/1990 | Bohannan |
| 4,991,433 A | | 2/1991 | Warnaka et al. |
| 5,040,423 A | | 8/1991 | Gould |
| 5,054,327 A | | 10/1991 | Gould |
| 5,226,604 A | | 7/1993 | Seiffert et al. |
| 5,241,859 A | * | 9/1993 | Smith ........................ 73/152.18 |
| 5,370,195 A | | 12/1994 | Keshavan et al. |
| 6,175,536 B1 | * | 1/2001 | Khan ............................. 367/32 |
| 6,364,837 B1 | | 4/2002 | Mazes et al. |
| 6,782,970 B2 | * | 8/2004 | Chang ........................... 181/101 |
| 6,938,488 B2 | | 9/2005 | Diaz et al. |
| 7,017,677 B2 | | 3/2006 | Keshavan et al. |
| 7,387,021 B2 | | 6/2008 | DiFoggio |
| 7,458,257 B2 | | 12/2008 | Pop et al. |
| 7,516,655 B2 | | 4/2009 | DiFoggio |
| 7,520,158 B2 | | 4/2009 | DiFoggio |
| 7,546,888 B2 | | 6/2009 | Cruz |
| 7,752,906 B2 | | 7/2010 | Pop et al. |
| 8,056,408 B2 | | 11/2011 | Pop et al. |
| 8,082,105 B2 | | 12/2011 | Ryu et al. |
| 8,127,621 B2 | | 3/2012 | Breen et al. |
| 8,234,912 B2 | | 8/2012 | Suarez-Rivera et al. |
| 2003/0106995 A1 | * | 6/2003 | Smith ................... E21B 49/005 250/282 |
| 2003/0178515 A1 | | 9/2003 | Boerhout et al. |
| 2004/0035208 A1 | * | 2/2004 | Diaz et al. ...................... 73/597 |
| 2006/0266108 A1 | * | 11/2006 | DiFoggio .................. 73/152.47 |

FOREIGN PATENT DOCUMENTS

| | | |
|---|---|---|
| WO | WO 2007/092527 | 8/2007 |
| WO | 2008/054118 | 5/2008 |

OTHER PUBLICATIONS

Fischer, Mark P., et al., (1996), "Fracture Toughness of Ice and Firn Determined From the Modified Ring Test,", *Journal of Glaciology*, vol. 41, No. 138, pp. 383-394.

Arasteh, M.M, et al (1997) "Broadband Acoustic Emission Observations During Fracture Propagation in Rock-like Material", *International Journal of Rock Mechanics and Mining Sciences*, vol. 34, p. 634.

Butt, S.D., et al. (1999), "Development of an apparatus to study the gas permeability and acoustic emission characteristics of an outburst-prone sandstone as a function of stress" *International Journal of Rock Mechanics and Mining Sciences*, vol. 36, pp. 1079-1085.

Deflandre, J.P. (1989) "Laboratory Analysis of Acoustic Emission Associated With the Hydraulic Fracturing of Sandstone Samples" *Revue de L'Institut Francais du Petrole Septembre-Octobre*, No. 5, Paris, FR pp. 673-691.

\* cited by examiner

SYSTEMS AND METHODS FOR DETERMINING GEOLOGIC PROPERTIES USING ACOUSTIC ANALYSIS

CROSS-REFERENCE TO RELATED APPLICATION

This application is the Continuation of U.S. patent application Ser. No. 12/992,844 which is the National Stage of International Application No. PCT/US09/041128, filed on 20 Apr. 2009, which claims the benefit of U.S. Provisional Application No. 61/080,339, filed 14 Jul. 2008 entitled SYSTEMS AND METHODS FOR DETERMINING GEOLOGIC PROPERTIES USING ACOUSTIC ANALYSIS, the entirety of which is incorporated by reference herein.

TECHNICAL FIELD

The present invention relates to determining geologic properties and, more particularly, to determining geologic properties using acoustic analysis.

BACKGROUND OF THE INVENTION

It is often useful to determine properties of various rock formations, such as to determine the porosity, permeability, and/or composition of rock formations. For example, it is desirable to determine properties of rock formations encountered during drilling of hydrocarbon exploration and production wells so as to provide information with respect to the ability of the rock formations to store hydrocarbon reserves and/or the ability of the rock formations to allow fluids to flow through them. To optimize well completion strategies, the lithology and mineralogy of the rock formations are important.

In all rocks the physical strength of the rock is related to the minerals found in the rock, the pore structure, and the cementation of the rock. In fine grained clastic rocks, such as conglomerate, sandstone, siltstone, and shale, the sealing capacity of the rock is related to silt content, wherein the sealing capacity parameter (e.g., capillary entry pressure) controls whether the rock can hold a hydrocarbon column below it now or in the geological past. Parameters such as fraccability are related to silt or quartz content of fine grained siliciclastic rocks. Accordingly, well fracturing strategies for tight shale gas may be limited to particular mineralogies, such as rock formation zones with high quartz content, in order to deliver more effective fracture length.

To determine various rock properties, quantitative mineralogical compositions of rock samples are often needed. For example, quantitative X-Ray diffraction techniques may be utilized with respect to rock samples to determine mineralogy. However, such analysis is generally relatively expensive and often time-consuming, requiring on the order of days or weeks to complete the analysis. Conventional or sidewall core samples are traditionally needed to determine some rock properties, such as rock porosity and permeability. Such samples are costly and often it is not possible to obtain core samples, such as where a lack of well bore stability does not permit the removal of the drill string for insertion of a core sample collection tool. Using such core samples, when available, porosity and permeability may be determined in specialized laboratories through application of confining stresses in costly and time consuming procedures.

It is possible to measure, often indirectly, some rock properties using well-logging tools, such as wireline logging tools. However, running such logging tools is expensive, time consuming and sometimes not possible, such as due to well bore instability.

It can be appreciated from the foregoing that the presently available techniques for determining various properties of rock formations are generally expensive and time-consuming. Moreover, irrespective of cost and time required to make the determinations, many such techniques are often not available in particular situations.

BRIEF SUMMARY OF THE INVENTION

The present invention is directed to systems and methods which determine geologic properties using acoustic analysis. Acoustic signals are collected during processing of geologic media, such as rock samples, for determining geologic properties according to embodiments of the invention. Processing of geologic media from which acoustic signals may be collected according to embodiments of the invention include crushing, shearing, striking, compressing, etc. geologic media. The acoustic signals collected during such processing may include frequency information, amplitude information, time information, etc. which may be utilized in determining geologic properties according to embodiments of the invention. Geologic properties which may be determined using acoustic analysis according to embodiments of the invention include geologic media properties such as mineralogy, porosity, permeability, sealing capacity (e.g., capillary entry pressure), fracability, compressive strength, compressibility, Poisson's Ratio, Youngs Modulus, Bulk Modulus, Shear Modulus, and/or the like. Geologic properties may additionally include geologic structure properties, such as lithology, seal quality, reservoir quality, etc., as may be estimated from determined geologic media properties of a plurality of samples. Additionally or alternatively, geologic properties in addition to or in the alternative to geologic media properties and/or geologic structure properties may be provided according to embodiments of the invention, such as to provide geologic acoustic properties of the geologic media, such as acoustic logging effectiveness, acoustic response, natural or harmonic frequencies, and/or the like, as may be useful in determining if acoustic logging tools are to be utilized with respect to a well or region etc.

Embodiments of the present invention may be used to provide determination of geologic properties from a variety of geologic media samples, including geologic media samples which are generally considered of poor quality or which are not otherwise obtained specifically for the purpose of analysis. For example, rock cuttings obtained from well drilling activity, rather than core samples obtained for rock formation analysis, may be utilized according to embodiments of the invention.

Processing of geologic media, such as crushing geologic media samples, may be performed for the purpose of capturing of acoustic signals for analysis according to embodiments of the invention. However, preferred embodiments of the invention operate to capture acoustic signals for analysis during processing of geologic media for other purposes. For example, geologic media samples may be processed in a crushing chamber under a vacuum to provide fluid inclusion volatiles (FIV) analysis, wherein volatile components trapped in micro cavities or fluid inclusions in mineral grains are released and analyzed by mass spectrometry. One or more acoustic sensor may be disposed in or on a FIV crushing chamber, or in communication therewith, to obtain acoustic signals during FIV processing operation for analysis and determination of geologic media properties according to embodiments of the invention.

Irrespective of whether geologic media processing is provided for the purpose of capturing acoustic signals or for other purposes, such processing is expected to take on the order of a few minutes to complete, according to embodiments of the invention. Accordingly, embodiments of the invention facilitate a large number of geologic media samples to be analyzed in a short period of time, such as on the order of 500-600 samples in a day.

Embodiments preferably provide relatively rapid data collection and analysis to facilitate providing determination of geologic properties with respect to a large number of geologic media samples, such as to provide analysis of geologic media over entire well intervals, and/or to provide geologic property determinations with relatively little delay from sample collection, such as to provide near real-time analysis during well drilling operations. Geologic property data provided according to embodiments of the invention is timely to the point that log interpretation and down hole logging tool selection may be impacted, such as in determining whether and what types of down hole logging tools are to be utilized during well drilling operations. Additionally or alternatively, geologic property data provided according to embodiments of the invention may be used for such purposes as guiding well completion decisions, reservoir production decisions, exploration decisions, etc.

Acoustic emission signatures, which are related to the properties of the geologic media samples, generated during geologic media processing are analyzed for determination of specific properties of the geologic media according to embodiments of the invention. For example, such acoustic emission signatures may be compared to a database of acoustic emission signatures, or portions thereof, generated from known exemplars for determinations with respect to inclusion of particular properties in the processed geologic media. Such acoustic emission analysis may be performed in an automated fashion through use of appropriate computer logic (e.g., software code, application specific integrated circuits (ASICs), special purpose logic circuitry, etc.) to provide rapid analysis of geologic media.

Geologic properties may be determined continuously throughout a well and displayed or presented in a robust fashion, such as to present the information in a chart similar to a well log. The information provided according to embodiments of the invention may be compared and mapped throughout areas of interest, such as using information associated with a plurality of wells.

From the above, it can be appreciated that embodiments of the invention provide rapid and abundant geologic property data. Moreover, embodiments provide geologic property data inexpensively, both with respect to the time, tools, and equipment used in the technique and in the ability to leverage geologic media processing performed for other purposes. According to some embodiments, robust geologic property information is yielded where core samples and/or logging information are not available.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

Figure 1:
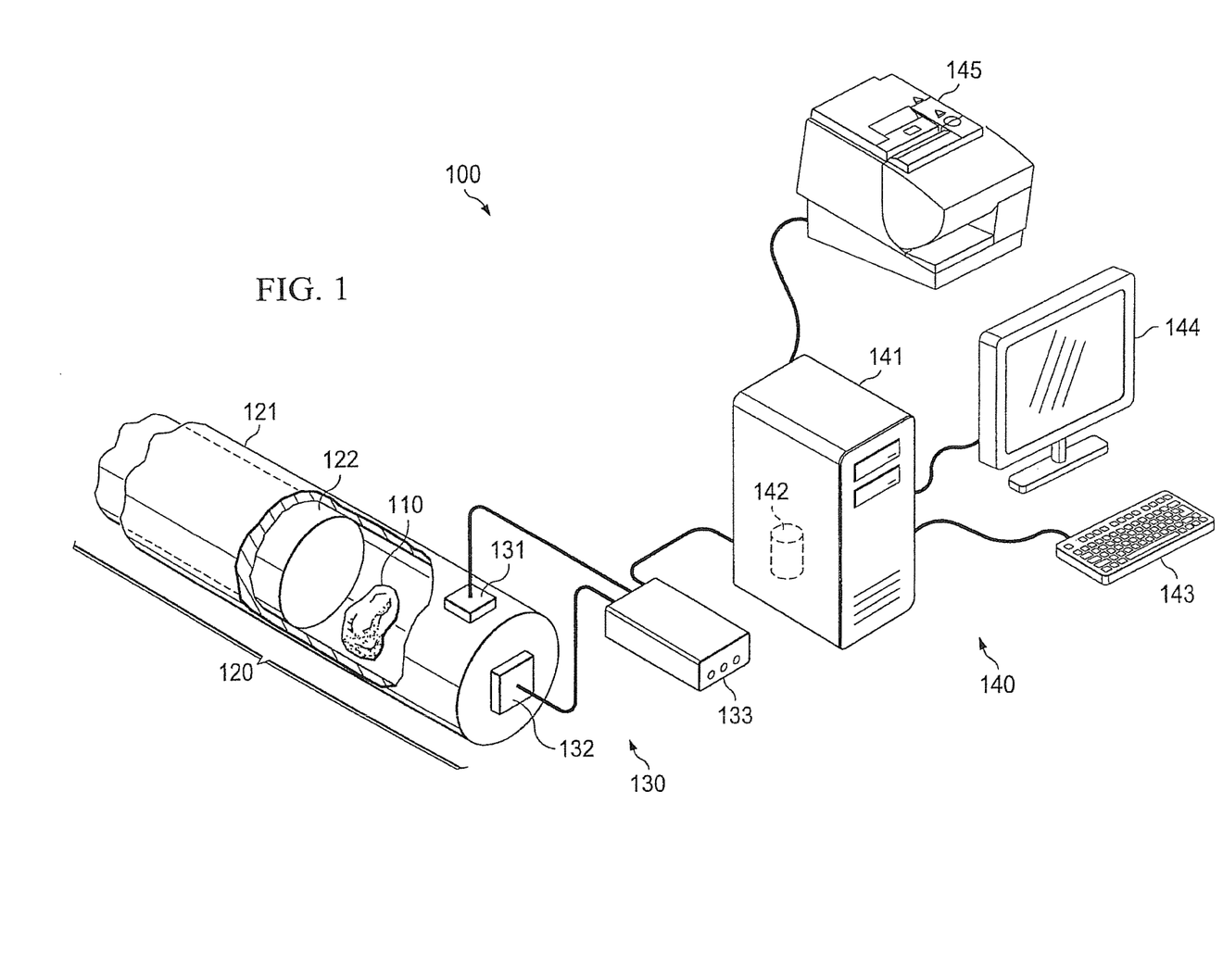
FIG. 1 shows a system adapted for determining geologic properties using acoustic analysis according to an embodiment of the invention.

Directing attention to FIG. 1, a system adapted for determining geologic properties using acoustic analysis is shown as system 100. System 100 of the illustrated embodiment includes geologic media processing system 120, acoustic signal acquisition system 130, and acoustic analysis system 140 adapted to provide operation as described herein. To aid in understanding the concepts of the present invention, embodiments of system 100 will be described herein with reference to determining geologic properties with respect to regions associated with hydrocarbon exploration and/or production. Accordingly, embodiments are described with reference to determining rock properties using rock samples, such as rock cuttings, available from hydrocarbon exploration and/or production wells. It should be appreciated that the concepts of the present invention are not limited to this form of geologic media and are not limited to use with respect to regions associated with hydrocarbon exploration.

Geologic media processing system 120 of the illustrated embodiment processes geologic media samples, such as rock sample 110 (e.g., a rock cutting, a core sample, a whole piece of rock, etc.), resulting in acoustic energy emanating from the sample. Geologic media processing utilized according to embodiments of the invention may comprise crushing, shearing, striking, compressing, etc. the sample. In the illustrated embodiment, for example, ram 122 may be driven, such as by a hydraulic or pneumatic cylinder (not shown), into chamber 121 in which rock sample 110 is disposed to thereby compress or crush rock sample 110.

Geologic media processing is preferably provided in a controlled and predetermined manner so as to facilitate meaningful comparison and analysis of one or more parameters of acoustic energy emitted from different samples. For example, ram 122 may be controlled to impart a predetermined amount of pressure for a predetermined amount of time upon a sample disposed in chamber 121. Processing of geologic media utilized according to embodiments of the invention may include various steps, techniques, etc. For example, ram 122 may be controlled to impart a first predetermined amount of pressure for a predetermined amount of time, a second predetermined amount of pressure for a predetermined amount of time, and a third predetermined amount of pressure for a predetermined amount of time while acoustic energy from each such step is collected to provide acoustic analysis as described herein. Additionally or alternatively, different techniques (e.g., shearing a sample and crushing the sample), may be implemented for a sample while collecting acoustic energy from each such technique to provide acoustic analysis according to embodiments.

Geologic media processing provided by geologic media processing system 120 may be performed expressly for the purpose of obtaining acoustic energy for analysis, if desired. However, embodiments of the invention operate to obtain acoustic energy for analysis during processing of geologic media for other purposes. For example, rock sample 110 may comprise a rock cutting from a well currently being drilled, wherein rock sample 110 is being processed in geologic media processing system 120 to provide fluid inclusion volatiles (FIV) analysis. It was noticed by the present inventors that, as the rock samples are crushed and vapor releases, sound and vibration are also generated. Accordingly, geologic media processing system 120 may comprise a FIV system.

During FIV processing, rock samples are crushed in an evacuated chamber, releasing volatile components trapped in micro cavities or fluid inclusions in mineral grains that are analyzed by mass spectrometry. For example, samples may be crushed via a piston system that impinges on the samples 3 times per sample over a standard set of pressures and time. In such an embodiment, chamber 121 may comprise a crushing chamber under a vacuum, wherein volatile components trapped in micro cavities or fluid inclusions in mineral grains are released and analyzed by a mass spectrometer (not shown). Acoustic energy emitted by crushing of rock sample 110 during FIV analysis may be collected for analysis according to embodiments of the invention.

Acoustic signal acquisition system 130 of the illustrated embodiment comprises sensors 131 and 132 in communication with geologic media processing system 120 and signal conditioning unit 133. Sensors 131 and 132 obtain acoustic energy emitted through operation of geologic media processing system 120 and provide corresponding acoustic signals (e.g., analog or digital electrical signals) to signal conditioning unit 133. Accordingly, sensors 131 and 132 are preferably attached to or disposed within one or more surface of chamber 121 and/or ram 122. For example, sensors utilized according to embodiments of the invention may be disposed upon an exterior surface (such as through use of magnetic attraction, adhesive, fasteners, etc.) of chamber 121 or ram 122, where chamber 121 is comprised of a metallic body or other adequate conductor of sound energy. Additionally or alternatively, sensors utilized according to embodiments of the invention may be embedded into a surface (such as through use of through-holes, receiver cavities, lamination, molding, etc.) of chamber 121 or ram 122 or disposed within a processing area (such as in a recess of a processing chamber etc.), if desired. One or more sensors utilized according to embodiments may preferably be disposed as close to the media processing area to improve captured samples, such as to improve signal to noise, avoid distortion, minimize interference, etc.

Sensors 131 and 132 of embodiments comprise acoustic transducers, such as may be embodied in sound, pressure, and/or vibration transducers. The particular transducer used and its configuration can vary depending upon the samples to be processed, the properties to be determined, the type of processing performed with respect to the samples, etc. However, embodiments of the invention, wherein rock cuttings from well drilling operations are crushed, utilize one or more sensors providing a frequency bandwidth of greater than 10 kHz. For example, one or more piezoelectric accelerometers, such as the B&K 4384 accelerometer or other models available from Brüel and Kjær, Skodsborgvej, Denmark, may be used to capture acoustic energy in a frequency band of approximately 5,000 to 20,000 Hz. Such acoustic energy may be captured by a single sensor having sufficient bandwidth to capture energy over the foregoing frequency band. Additionally or alternatively, the acoustic energy may be captured by a plurality of sensors, each having insufficient bandwidth to capture energy over the foregoing frequency band, which when used together cooperate to capture energy over the foregoing frequency band. Experimentation has revealed that, at least in some situations, higher frequencies (e.g., frequencies above 20,000 Hz or even frequencies in the range generally considered ultrasonic) present more and/or better information about rock properties. Accordingly, one or more sensors utilized according to embodiments of the invention operate to capture such frequencies.

Although particular example configurations of sensors have been described above to aid in understanding the concepts of the present invention, it should be appreciated that embodiments of the present invention may implement any configuration of sensor suitable for providing signals corresponding to acoustic energy emitted by samples being processed. For example, a plurality of sensors operable to collect acoustic energy through different techniques (e.g., one sensor using pressure and another sensor using vibration) may be used. Sensors collecting acoustic energy using different techniques may be disposed for use differently according to embodiments of the invention. For example, whereas sensors responsive to vibration may be disposed on an exterior surface of a processing chamber, sensors directly responsive to sound may be disposed within a processing chamber. Ultra-high frequency transducers, such as acoustic emission sensors and/or ultrasonic sensors may be used to collect the acoustic energy of frequency bands beyond audio range. Sensors used according to embodiments of the invention may provide collection of acoustic energy in non-overlapping, partially overlapping, and/or fully overlapping operating bands. For example, a first sensor, having a relatively narrow frequency bandwidth, may operate to collect acoustic energy at a first center frequency while a second sensor, having a relatively narrow frequency bandwidth, may operate to collect acoustic energy at a second center frequency, wherein the narrow bandwidths aggregate to provide sampling of a desired, broader bandwidth.

Signal conditioning unit 133 of the illustrated embodiment accepts acoustic signals corresponding to acoustic energy as sensed by sensors 131 and 132 and provides output of conditioned acoustic signals for further processing by acoustic analysis system 140. Accordingly, signal conditioning unit 133 of embodiments comprises one or more amplifier, filter, attenuator, and/or the like adapted to enhance, modify, or change attributes of acoustic signals as appropriate or desired for providing signals to acoustic analysis system 140. For example, signal conditioning unit 133 may comprise one or more bandpass filter having cutoff frequencies to prevent passing signal energy outside of a bandwidth sampled by sensors 131 and 132. Additionally or alternatively, signal conditioning unit 133 may comprise one or more bandstop filter (e.g., notch filter) having a center frequency selected to prevent passing signal energy associated with a particular sound source or other known or expected interference. Other filter configurations may be utilized as part of signal conditioning unit 133, such as high pass, low pass, adjustable (e.g., tracking), analog, and digital filters, and noise cancellers. Similarly, other circuitry may be utilized as part of signal conditioning unit 133, such as low noise amplifiers, variable gain amplifiers, variable attenuators, analog to digital converters, digital to analog converters, interference cancellers, mixers (e.g., frequency translation circuitry), and/or the like.

Although illustrated separately, it should be appreciated that the functionality of signal conditioning unit 133 may be integrated into one or more components of system 100. For example, filtering, amplification, and/or attenuation may be provided by sensors 131 and 132, acoustic analysis system 140, or a combination thereof, to thereby integrally provide signal conditioning of signal conditioning unit 133.

Figure 2:
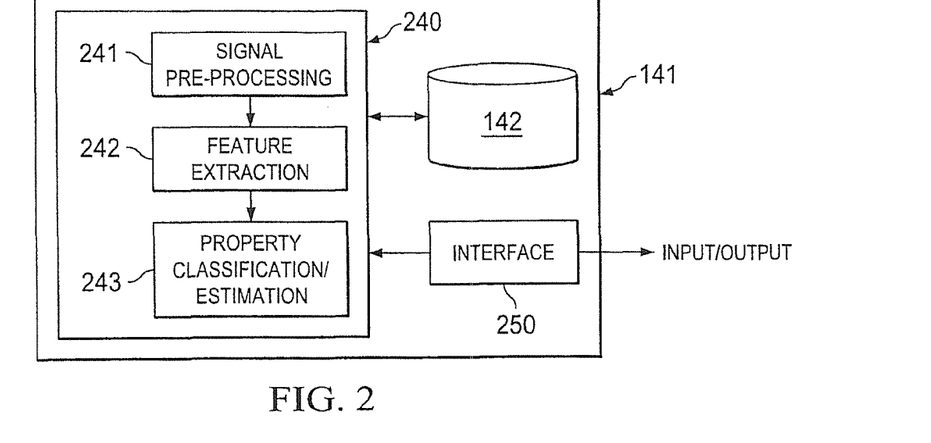
FIG. 2 shows functional blocks of an instruction set operable with respect to the system of FIG. 1 to provide geologic property determination using acoustic analysis according to an embodiment of the invention.

Acoustic analysis system 140 of the illustrated embodiment includes processor-based system 141 in communication with signal conditioning unit 133. Processor-based system 141 preferably includes one or more processors (not shown), such as a central processing unit (CPU) from the PENTIUM family of processors available from Intel Corporation or from the POWERPC family of processors available from the AIM alliance (Apple-IBM-Motorola), operable under control of an instruction set (e.g., software 240 of FIG. 2) defining operation as described herein. Referring to FIG. 2, software 240 of an embodiment of the present invention is shown to include various functional blocks operable with respect to processor-based system 141 to provide operation as described herein. Specifically, software 240 of FIG. 2 includes signal pre-processing 241, feature extraction 242, and property classification/estimation 243, as will be discussed in further detail below.

Processor-based system 141 of embodiments includes memory, such as may comprise random access memory (RAM), read only memory (ROM), disk memory, optical memory, flash memory, and/or the like. For example, the illustrated embodiment of processor-based system 141 includes memory in the form of database 142, such as may be utilized to store acoustic signals, acoustic signatures, instruction sets, test parameters, test results, etc. Processor-based system 141 of the illustrated embodiment is further coupled to various input/output devices, shown here as keyboard 143, display 144, and printer 145. Keyboard 143, display 144, and printer 145 provide a user interface wherein a user may interact with processor-based system 141 to input data, instructions, commands, etc. (e.g., via keyboard 143) and to obtain data, images, results, information, etc. (e.g., transiently via display 144 and substantially permanently via printer 145).

User interface devices in addition to or in the alternative to those shown may be utilized according to embodiments. For example, embodiments may utilize various pointing devices, such as a mouse, a touch screen, and a digitizing tablet, aural output devices, such as speakers, aural input devices, such as microphones, etc. Processor-based system 141 may additionally or alternatively utilize devices or components other than user interface devices, such as network interface cards (NIC) (e.g., for communication via the Internet, an intranet, an extranet, a local area network (LAN), a metropolitan area network (MAN), a wide area network (WAN), a wireless network, etc.), modems (e.g., for providing communication via the public switched telephone network (PSTN), a cable transmission system, etc.), co-processors (e.g., for providing accelerated or enhanced mathematical operations, graphical rendering, etc.), and interfaces (e.g., for providing analog to digital conversion, digital to analog conversion, protocol conversion, etc.).

It should be appreciated that system 100 may be provided in a number of configurations which are operable as described herein. For example, a portable implementation of geologic media processing system 120 (e.g., suitably small and light weight, powered by a source which is readily available at expected operational sites, such as a well site) may be provided for coupling to a portable implementation of acoustic analysis system 140 (e.g., a laptop computer configuration) for use in in-situ acoustic measurement and analysis (e.g., where the information on rock properties is needed while drilling).

Figure 3:
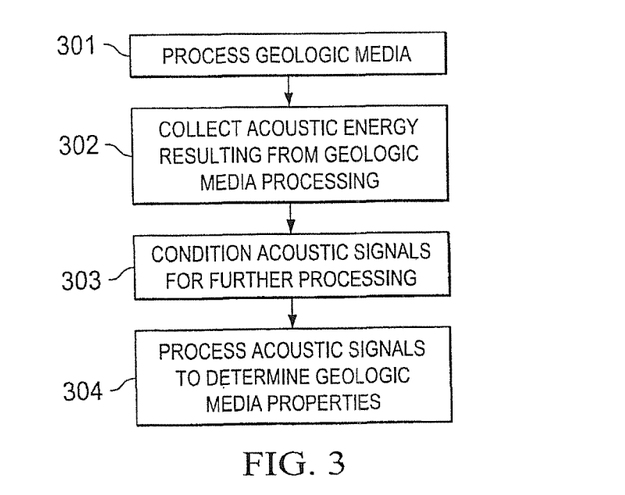
FIG. 3 shows a flow diagram of operation providing geologic property determination using acoustic analysis according to an embodiment of the invention.

Directing attention to FIG. 3, operation of system 100 according to an embodiment for determining geologic properties using acoustic analysis is shown. At block 301, one or more geologic media sample such as rock sample 110 is processed. For example, rock sample 110 may be disposed within chamber 121 and ram 122 activated to provide crushing pressure thereto. As rock sample 110 is processed, acoustic energy is emitted therefrom. According to embodiments of the invention, one or more geologic media processing parameters (e.g., the crushing force and duration) are adapted to maximize or optimize the information in resulting acoustic emissions. At least a portion of this acoustic energy (e.g., the frequency, amplitude, decay rate, etc.) is related to or a result of properties of the sample (e.g., mineralogy, porosity, permeability, sealing capacity, fracability, compressive strength, compressibility, Poisson's Ratio, Youngs Modulus, Bulk Modulus, Shear Modulus, etc.).

Figure 4A:
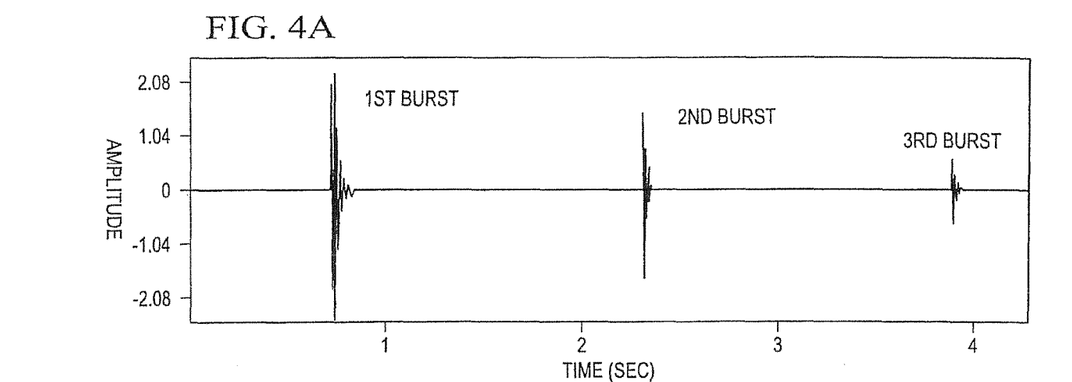
FIGS. 4A and 4B show graphical representations of acoustic emissions as may be utilized to provide geologic property determinations according to embodiments of the invention.
Figure 4B:
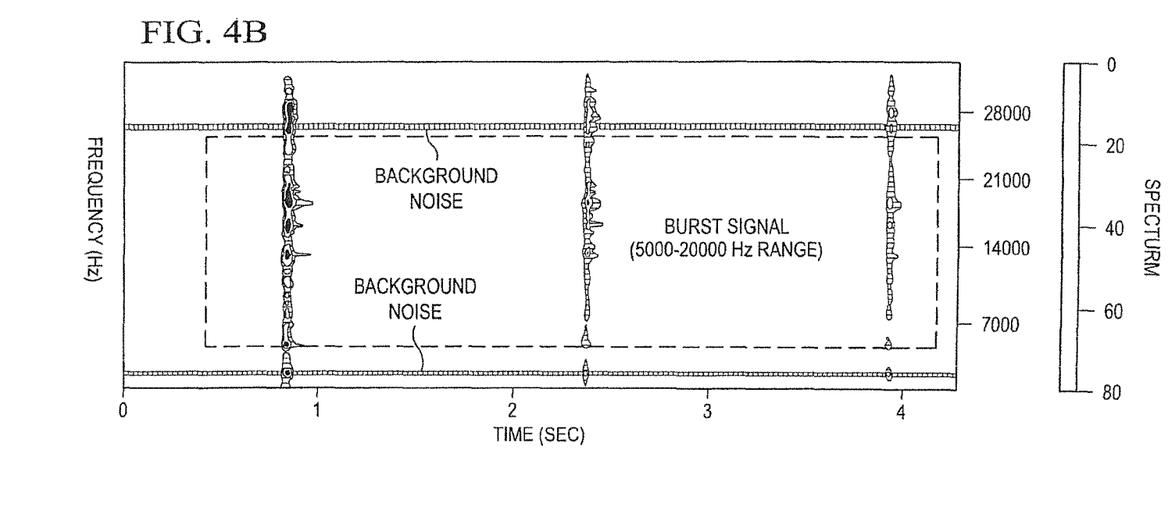

FIGS. 4A and 4B show an example of acoustic emission of an exemplary sand sample as processed using a process wherein 3 crushing pressures are applied to the sample (e.g., FIV processing). Specifically, FIG. 4A shows the resulting acoustic signal in the time domain (e.g., vibration amplitude verse time) and FIG. 4B shows a frequency spectrogram of the resulting acoustic signal (e.g., vibration amplitude and frequency verse time). As can be seen, a broad spectrum of frequencies and amplitudes are emitted during the process, although it should be appreciated that the unprocessed acoustic signal typically includes background vibration (e.g., due to auxiliary equipment such as motor and pump operation, valve closing and opening, etc.) in addition to acoustic emissions associated with equipment impacting the sample and the sample breaking-up.

At block 302, acoustic energy resulting from geologic media processing is collected. For example, sensors 131 and 132 may operate to convert vibrations, sound, changes in pressure, etc. into corresponding electrical signals. Such electrical signals preferably include information regarding frequency, amplitude, and/or timing. Electrical signals provided as a result of collecting acoustic energy from geologic media processing according to embodiments of the invention may comprise analog signals and/or digital signals, as appropriate for further processing according to embodiments of the invention.

At block 303 of the illustrated embodiment, conditioning is provided with respect to acoustic signals resulting from acoustic energy collection at block 302. For example, signal conditioning unit 133 of embodiments operates to receive electrical signals from sensors 131 and 132 and to enhance, modify, and/or change attributes of the signals as appropriate or desired for further processing. In operation according to embodiments, signal conditioning unit 133 may amplify, filter, and/or attenuate signals, such as to improve the signal to noise ratio, before passing the signals to acoustic analysis system 140. Acoustic signals as conditioned by signal conditioning unit 133 of the illustrated embodiment are passed for processing to determine geologic properties.

At block 304, acoustic signals are processed to determine geologic properties. For example, acoustic analysis system 140 receives acoustic signals from signal conditioning unit 133 and processes the signals to determine geologic properties of the sample itself (e.g., geologic media properties such as mineralogy, porosity, permeability, sealing capacity, fracability, compressive strength, compressibility, Poisson's Ratio, Youngs Modulus, Bulk Modulus, Shear Modulus, etc.), geologic properties of a region from which the sample was taken (e.g., geologic structure properties such as lithology, seal quality, reservoir quality, etc.), as may be estimated from determined geologic properties. Additionally or alternatively, geologic property information in addition to or in the alternative to geologic media properties and/or geologic structure properties may be provided according to embodiments of the invention, such as to provide geologic acoustic properties of the geologic media as may be useful in determining if acoustic logging tools are to be utilized with respect to a well or region.

Processing of acoustic signals to determine geologic properties according to embodiments of the invention is provided through operation of software 240 (FIG. 2) executing upon processor-based system 141. Software 240 preferably comprises data analysis and decision-making algorithms to classify the samples and estimate the geologic properties. Accordingly, software 240 of the illustrated embodiment includes signal pre-processing 241, feature extraction 242, and property classification/estimation 243 cooperating to provide processing of acoustic signals for determining geologic properties.

It should be appreciated that software 240 or portions thereof (e.g., signal pre-processing 241, feature extraction 242, and/or property classification/estimation 243) may utilize various resources of processor-based system 141 and/or resources in communication therewith in providing operation as described herein. For example, one or more functional blocks of processor-based system 141 may utilize a NIC (e.g., for communication via the Internet, an intranet, an extranet, a LAN, a MAN, a WAN, a wireless network, etc.), a modem (e.g., for providing communication via the PSTN, a cable transmission system, etc.), a co-processor (e.g., for providing accelerated or enhanced mathematical operations, graphical rendering, etc.), an interface (e.g., for providing analog to digital conversion, digital to analog conversion, protocol conversion, input/output, etc.), and/or a peripheral (e.g., for user interface, data storage, data retrieval, etc.). An interface such as may provide analog to digital conversion of acoustic signals from sensors 131 and 132 and/or signal conditioning unit 133, input of data from keyboard 143, output of data to display 144, output of data to printer 145, and/or other input/output interfacing useful according to embodiments is shown as interface 250 in the illustrated embodiment.

Signal pre-processing 241 preferably accepts acoustic signals, such as those provided by sensors 131 and 132 and/or signal conditioning unit 133, and provides mitigation of artifacts in the acoustic signals not associated with sample properties, or which are otherwise not desirable (e.g., background noise). For example, acoustic energy associated with the operation of a hydraulic pump, ram actuator, valve operation, etc. may be present during processing of geologic media. Noise cancellation techniques may be implemented by signal pre-processing 241 to remove such artifacts, such as by digitally providing an out of phase signal at the appropriate frequency and amplitude to cancel the noise. Additionally or alternatively, filters specifically tuned for particular acoustic artifacts may be implemented (e.g., digitally), perhaps at appropriate times, to remove or mitigate such artifacts in the signals as passed for further processing. It should be appreciated that signal conditioning and pre-processing as provided by signal processing unit 133 and signal pre-processing 241 may be consolidated or distributed as appropriate for any particular implementation.

Feature extraction 242 preferably operates to identify and/or extract relevant features of the pre-processed signals. For example, feature extraction 242 may operate to identify and extract features relevant to acoustic emission signatures, such as dominant acoustic frequencies and/or amplitudes, frequency and/or amplitude profiles, energy profiles across a frequency band and/or for particular frequencies, decay rates, burst energies, duration of each crushing for multiple crushing tests, parameters of dominant wavelets, and/or the like. Feature extraction 242 of embodiments may thus operate to analyze acoustic signals, e.g., continuously and/or instantaneously, to identify various features thereof. Such feature identification is preferably performed through either short-time frequency analysis or/and wavelet analysis on the pre-processed signals. Once identified, portions of the acoustic signals having features of interest may be extracted or otherwise isolated for further analysis. For example, optimal features may be selected from training data sets, such as acoustic energy distribution over different frequency bands, wherein such optimal features are selected to minimize errors of rock property classification and estimation. The optimal features may be utilized to identify features of interest for extraction within the pre-processed signals. Extracted features are preferably passed to other functional blocks of software 240 for analysis as described herein.

Property classification/estimation 243 operates to analyze features extracted by feature extraction 242 to estimate geologic properties. For example, property classification/estimation 243 may utilize a data correlation model to map the features of the acoustic emissions to physical properties such as rock lithology, composition, porosity, and elastic modulus. In operation according to embodiments of the invention, property classification/estimation 243 may compare features of the acoustic emissions to a database of features, such as stored in database 142, to associate particular properties with the sample. For example, samples having known properties (whether known pure samples (e.g., pure pyrite, quartz, calcite, dolomite, etc.), known aggregates, known compositions, known physical structure, etc.) may have been processed (e.g., using system 100 in accordance with the process of FIG. 2) to collect exemplary feature signatures. Such exemplary feature signatures may be stored in database 142 in association with information regarding their known properties, such as to provide property correlation models. Correlation models utilized according to embodiments of the invention may comprise empirical model such as multivariate regression, classification tree, principle component analysis, Bayesian belief networks, linear discriminant analysis, support vector machines, neural network, and/or other type of models.

Building correlation models according to embodiments of the invention may utilize a large number of samples with known or partially known properties. FIV analysis, providing processing of a large number of samples for other purposes, provides an opportunity for collecting a large amount of acoustic emission data with little additional cost. Using a database of acoustic signal features extracted from such high volume processing, data mining may be performed to create, revise, and/or modify correlation models useful according to embodiments of the invention.

A data correlation engine of property classification/estimation 243 may, using an appropriate correlation model, compare features extracted from acoustic signals emitted from processed samples having unknown properties to stored exemplary feature signatures to make determinations with respect to properties of the samples. That is, a correlation model is used by property classification/estimation 243 of embodiments that relates acoustic emission signature to the sample's properties. This correlation is based on assumption that different samples emit different sound when they are processed (e.g., different sounds emanate as different rock cuttings are broken-up under high impulse force). The mechanism generating the acoustic emission is complex. In microscopic view, a rock sample is generally composed of grains, pores, cement connecting the grains, etc. When subject to high compression stress, the compaction and dislocation of grains, braking up of cement, cracking and fracturing and ultimate failure of grains are possible sources of acoustic emission. Measured acoustic signature represents an aggregate of a variety of possible acoustic sources. The temporal pattern of the acoustic emission and detail frequency content may provide additional information of dominant acoustic sources at different stage of compression.

With a controlled stress condition in a confined chamber, as done in FIV processing, the acoustic emission is a function of physical properties of the rock sample. For example, a quartz grain is brittle and produces high intensity of sound when breaking up. With more quartz grains in a rock sample, the acoustic emission is expected to be higher when being compressed under high stress. The foregoing example of correlation of acoustic emission with quartz content in a rock sample is merely one of the possible correlations which may be made by operation of property classification/estimation 243 of embodiments. For example, other physical properties such as pore structure (pore size, pore geometry, porosity, and pore connectivity) and cement may also affect acoustic emission significantly for a particular sample with the same amount of quartz grains. Accordingly, embodiments of the invention, for example, relate the acoustic emission signature, statistically, with not only quartz content, but also with pore properties and permeability.

Correlation or other analysis of acoustic features to properties is not limited to analysis of a single feature signature. For example, variations in acoustic signal amplitude (such as at a particular frequency or the energy across the bandwidth of the acoustic signal) at different times during processing of a sample is utilized in geologic property analysis according to embodiments of the invention. Where FIV processing is performed such that samples are crushed via a piston system that impinges on the samples 3 times per sample over a standard set of pressures and time, variations in acoustic signal amplitude as between different ones of the 3 impingements of the piston (ram) upon a particular sample may be analyzed in determining the properties of the sample.

Additionally or alternatively, variations in acoustic signals as between different samples from a same source (e.g., a same well) may be used in analysis of the properties of individual samples (e.g., individual sample mineralogy) and/or properties of a region or area from which the samples were obtained (e.g., overall structure). For example, although particular acoustic feature signatures may be ambiguous (e.g., non-conclusive as between a plurality of properties) when considered alone, such acoustic feature signatures may be determinative when considered in combination with other acoustic feature signatures (whether from different samples from a same region or area or from the same sample). Moreover, property determinations made with respect to individual samples may be utilized together to provide a determination with respect to the properties of a larger region or area from which the samples were taken.

Operation of property classification/estimation 243 preferably provides output of determinations or estimations and/or other information regarding properties of the samples and/or a region or area with which they are associated. For example, property classification/estimation 243 may provide output regarding determinations with respect to geologic media properties (e.g., mineralogy, porosity, permeability, sealing capacity, fracability, compressive strength, compressibility, Poisson's Ratio, Youngs Modulus, Bulk Modulus, Shear Modulus, and/or the like), geologic structure properties (e.g., lithology, seal quality, reservoir quality, etc.), and/or geologic acoustic properties (e.g., acoustic logging effectiveness, acoustic response, natural or harmonic frequencies, etc.).

Figure 5:
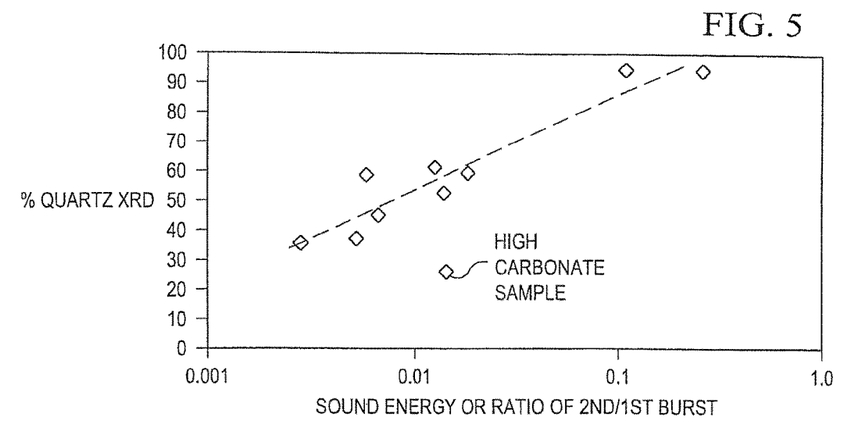
FIGS. 5, 6, 7A, and 7B show graphical representations of analysis of acoustic emission using correlation according to embodiments of the invention.

Directing attention to FIG. 5, a graphical representation of analysis of acoustic emission using correlation according to embodiments of the invention is shown. For the example of FIG. 5, cuttings from well drilling operations (e.g., from the Barnett Shale region) were processed using a process wherein 3 crushing pressures are applied to the sample (e.g., FIV processing) and the ratio of acoustic energy from the first crushing of a sample to the second crushing of the sample are correlated to quartz content. Accordingly, the X axis in FIG. 5 is the ratio of acoustic energy in the first crushing to that in the second crushing and the Y axis is the percentage of quartz, wherein the dotted line is a linear regression line with respect to the points plotted thereon (with the outlier, high carbonate, sample removed). The same samples were subject to quantative mineralogy analysis to determine the percentage of quartz in a more traditional way. It was found that there is a very strong correlation between the results of the traditional mineralogy analysis and the results provided by the graph of FIG. 5. Although one outlier is present in the data of FIG. 5, that particular sample was identified as having a very high carbonate content. Accordingly, further acoustic features may be analyzed with respect to such samples to provide more conclusive property determinations as described above.

Figure 6:
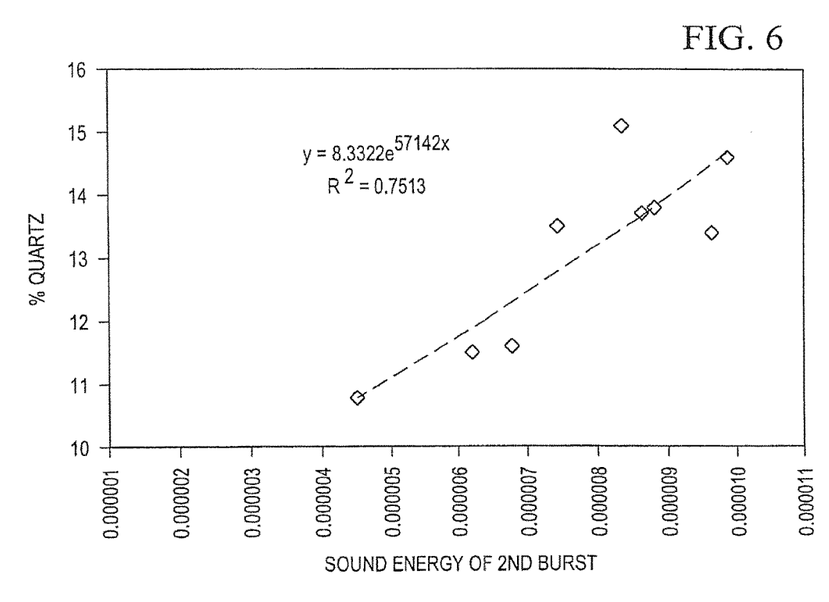

FIG. 6 shows another graphical representation of acoustic emission using correlation according embodiments of the invention. In the example of FIG. 6, cuttings from well drilling operations were processed using a processes wherein 3 crushing pressures are applied to the sample (e.g., FIV processing) and the total acoustic energy in the second crushing of samples correlated to quartz content. Accordingly, the X axis in FIG. 6 is the sound energy of the second crushing and the Y axis is the percentage of quartz, wherein the dotted line is a linear regression line with respect to the points plotted thereon. The same samples were subject to quantative mineralogy analysis to determine the percentage of quartz in a more traditional way. It was again found that there is a very strong correlation between the results of the traditional mineralogy analysis and the results provided by the graph of FIG. 6.

Figure 7A:
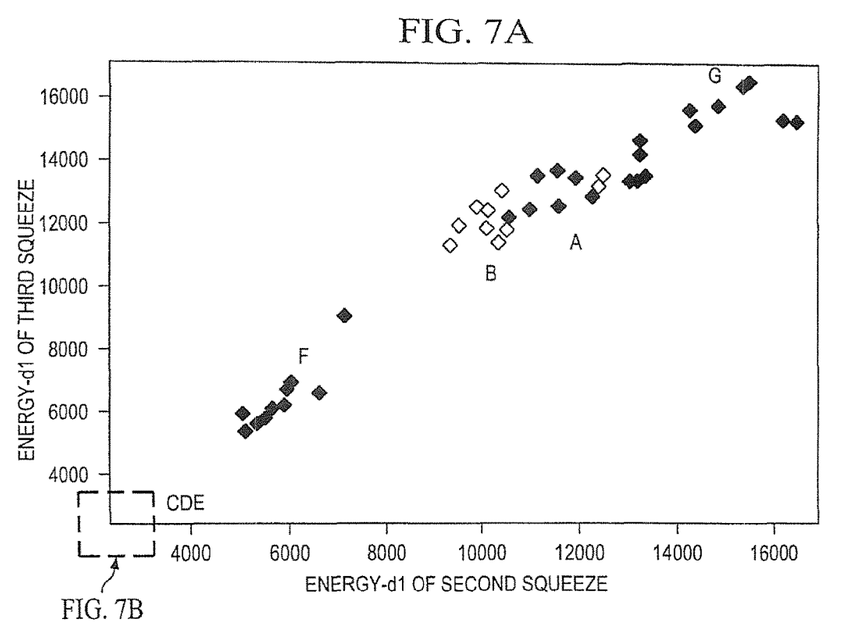
Figure 7B:
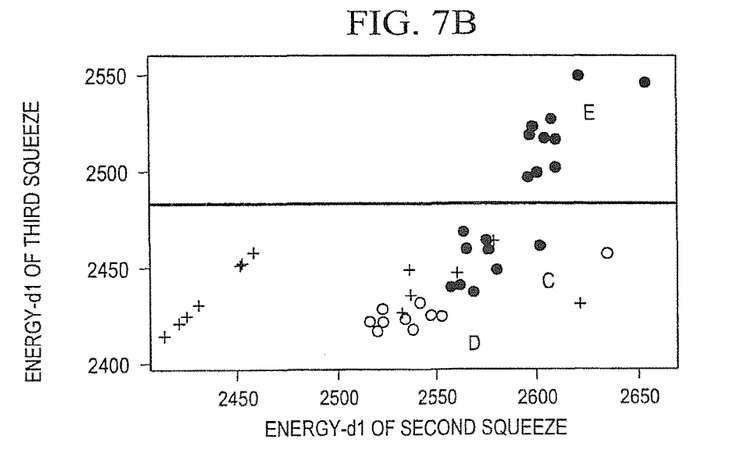

FIGS. 7A and 7B, wherein FIG. 7B provides enlarged detail with respect to a corresponding area of FIG. 7A, show yet another graphical representation of acoustic emission using correlation according to embodiments of the invention. In the example of FIGS. 7A and 7B, cuttings from well drilling operations were processed using processes wherein 3 crushing pressures are applied to the sample (e.g., FIV processing) and the acoustic energy in the second and third crushing are statistically analyzed to determine the mineralogical composition of the samples. Accordingly, the X axis in FIGS. 7A and 7B is the sound energy of the second crushing and the Y axis is the sound energy of the third crushing. As can be seen in the illustration, various clusters of points (shown here as clusters A, B, C, D, E, F, and G) become evident after a number of samples are processed It was found that there is a very strong correlation between a sample having a point from the total sound energy of the second and third crushing disposed in the area of one or more of these clusters and the mineralogy of the sample. Specifically it was found that samples having points in the regions of clusters A, B, and F contain sandstone, samples having points in the regions of clusters C and D comprise shale, samples having points in the region of cluster E comprise silty shale, and, samples having points in the regions of cluster G comprise sand.

From the above, it can be appreciated that acoustic emissions resulting from processing of geologic samples can be utilized to determine geologic properties (e.g., percent quartz present in the samples). Accordingly, embodiments of the invention provide a technique for determining geologic properties, such as mineralogical and physical properties of rock samples, through acoustic emission analysis. Such techniques are particularly useful in that the analysis may be performed relatively rapidly and at relatively low cost. Embodiments may, therefore, be used to provide analysis of rock types over entire well intervals. Moreover, in some cases embodiments of the invention may yield information where core samples or logging information is not available. Acoustic analysis according to embodiments of the invention may facilitate lithology, seal quality and reservoir quality properties to be estimated continuously throughout a well, perhaps displayed in a form similar to a well log. These indicators may be compared and mapped throughout areas of interest, and also used to guide completion decisions.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method comprising:
   processing a sample of geologic media for a primary purpose of fluid inclusion volatiles processing, wherein acoustic emissions are a byproduct of said processing;
   sampling acoustic emissions from said processing; and
   analyzing said sampled acoustic emissions to determine one or more geologic properties associated with said sample of geologic media, wherein said analyzing comprises analyzing a feature from a first sampled acoustic emission from said sample and a feature from a second sampled acoustic emission from said sample to determine a geologic property of said sample, wherein said geologic property comprises at least one of mineralogy, porosity, permeability, sealing capacity, fracability, compressive strength, compressibility, Poisson's Ratio, Youngs Modulus, Bulk Modulus, and Shear Modulus.

2. The method of claim 1, wherein said processing comprises:
   applying a crushing force to said sample.

3. The method of claim 1, wherein said processing comprises:
   applying a shearing force to said sample.

4. The method of claim 1, wherein said processing comprises:
   applying a striking force to said sample.

5. The method of claim 1, wherein said processing comprises:
   applying a compressing force to said sample.

6. The method of claim 1, wherein said sample comprises a cutting of said geologic media produced by a well drilling operation.

7. The method of claim 1, wherein said sample comprises a core sample of said geologic media produced using down-hole tools with respect to a well.

8. The method of claim 1, wherein said analyzing comprises:
   analyzing a plurality of features within a sampled acoustic emission from said sample to determine a geologic property of said sample.

9. The method of claim 1, wherein said analyzing comprises:
   analyzing a feature from a sampled acoustic emission from said sample and a feature from a sampled acoustic emission from another sample to determine a geologic property of said sample.

10. The method of claim 1, wherein said analyzing comprises:
    analyzing a feature from a sampled acoustic emission from said sample and a feature from a sampled acoustic emission from another sample to determine a geologic property of an area from which said sample and said another sample were obtained.

11. The method of claim 1, further comprising:
    processing said sampled acoustic emissions to remove artifacts in the acoustic signals not associated with sample properties.

12. A system comprising:
    an acoustic signal acquisition system coupled to a geologic media processing system and operable to obtain acoustic signals emitted during processing of sample geologic media by said geologic media processing system, wherein said geologic media processing system comprises a fluid inclusion volatiles processing system and wherein said geologic media processing system provides processing of said sample for a primary purpose of fluid inclusion volatiles processing and wherein said acoustic signals are a byproduct of said processing; and an acoustic analysis system in communication with said acoustic signal acquisition system and operable to analyze signals provided by said acoustic signal acquisition system to determine one or more geologic properties associated with said sample geologic media;

wherein said acoustic analysis system comprises a processor-based system operating under control of an instruction set operable to analyze said signals and determine said one or more geologic properties;

wherein said instruction set comprises a feature extraction module operable to identify one or more features within said signals provided by said acoustic signal acquisition system and a correlation engine operable to correlate said features to stored exemplary feature signatures.

13. The system of claim 12, wherein said acoustic signal acquisition system comprises:
at least one transducer selected from the group consisting of a sound transducer, a pressure transducer, and a vibration transducer.

14. The system of claim 12, wherein said acoustic signal acquisition system comprises:
at least one transducer disposed in a configuration selected from the group consisting of on a surface of said geologic media processing system, embedded in a structure of said geologic media processing system, and in a chamber of said geologic media processing system.

15. The system of claim 12, wherein said acoustic signal acquisition system comprises:
a signal conditioning circuit, wherein said signal conditioning circuit provides signal conditioning selected from the group consisting of signal amplification, signal filtering, signal attenuation.

16. The system of claim 12, wherein said processor-based system comprises:
a general purpose computer system.

17. A method comprising:
processing a sample of geologic media wherein said processing comprises one or more of applying a crushing force to said sample, applying a shearing force to said sample, applying a striking force to said sample, applying a compressing force to said sample, and fluid inclusion volatiles processing;

sampling acoustic emissions from said processing; and analyzing said sampled acoustic emissions to determine one or more geologic properties associated with said sample of geologic media, wherein the geologic properties comprise one or more of mineralogy, porosity, permeability, sealing capacity, fracability, compressive strength, compressibility, Poisson's Ratio, Youngs Modulus, Bulk Modulus, and Shear Modulus, wherein said analyzing comprises analyzing a feature from a first sampled acoustic emission from said sample and a feature from a second sampled acoustic emission from said sample to determine a geologic property of said sample; and wherein said processing comprises processing said sample for a primary purpose of fluid inclusion volatiles processing, wherein said acoustic emissions are a byproduct of said processing of said sample for said primary purpose.

* * * * *